United States Patent [19]

Kvam

[11] Patent Number: 4,824,866
[45] Date of Patent: Apr. 25, 1989

[54] ANTI-GLAUCOMA USE OF TRIFLUOROMETHANESULFONAMIDE

[75] Inventor: Donald C. Kvam, North Oaks, Minn.

[73] Assignee: Riker Laboratories, Inc., St. Paul, Minn.

[21] Appl. No.: 9,719

[22] Filed: Feb. 2, 1987

[51] Int. Cl.$^4$ .............................................. A61K 31/18
[52] U.S. Cl. ................................... 514/601; 514/605; 514/913
[58] Field of Search ................... 514/601, 605, 913

[56] References Cited

U.S. PATENT DOCUMENTS

| | | | |
|---|---|---|---|
| 2,732,398 | 1/1956 | Brice et al. | 260/503 |
| 3,609,187 | 9/1971 | Moore et al. | 260/556 F |
| 3,622,626 | 11/1971 | Moore | 260/556 F |
| 3,705,185 | 12/1972 | Moore et al. | 260/465 D |
| 4,438,123 | 3/1984 | Smith | 424/270 |
| 4,483,872 | 11/1984 | Barfknecht et al. | 514/603 |
| 4,619,939 | 10/1986 | Maren | 514/363 |

OTHER PUBLICATIONS

AMA Drug Evaluation-2ed (1973)-AMA Dept. of Drugs: Publishing Science Group Inc. pp. 675-686.

*Primary Examiner*—Douglas W. Robinson
*Attorney, Agent, or Firm*—Donald M. Sell; Walter N. Kirn; Robert W. Sprague

[57] ABSTRACT

Trifluoromethanesulfonamide and salts thereof are active as antiglaucoma agent and may be administered topically to the eye. Pharmaceutical formulations of such compounds are also described.

7 Claims, No Drawings

ANTI-GLAUCOMA USE OF TRIFLUOROMETHANESULFONAMIDE

TECHNICAL FIELD

This invention relates to a pharmaceutical treatment of glaucoma.

BACKGROUND OF THE INVENTION

Glaucoma is an ocular disorder associated with an elevated intraocular pressure which is too high for normal ocular function and may result in irreversible loss of visual function. If untreated, glaucoma may eventually lead to blindness. Ocular hypertension, that is, the condition of elevated intraocular pressure without optic nerve head damage or characteristic glaucomatous visual field defects, is now believed by many opthalmologists to represent the earliest phase of glaucoma.

Many of the drugs formerly used to treat glaucoma proved not entirely satisfactory. Indeed, few advances have been made in the treatment of glaucoma since pilocarpine and physostigmine were introduced for such treatment. Orally-administered carbonic anhydrase inhibitors are effective in some cases, and more recently topical beta-adrenergic blocking agents have been found to be effective in reducing intraocular pressure.

Although trifluoromethanesulfonamide and certain of its salts have been disclosed broadly in, for example, U.S. Pat. No. 2,732,398, Journal of the Chemical Society, 2640 (1957) and third International Fluorine Symposium, Munich (1965), their physiological activity as antiglaucoma agents has not previously been known.

Certain substituted haloalkanesulfonamides have previously been shown to have physiological activity as anticonvulsants. It has been theorized that since this activity is thought to be attributable to carbonic anhydrase activity, some of those compounds would also show activity against glaucoma. See U.S. Pat. Nos. 3,609,187, 3,622,626, and 3,705,185. However, prior art compounds, while they have been found to be active as antiglaucoma agents when administered orally, have been found to be inactive when administered topically.

BRIEF DESCRIPTION OF THE INVENTION

This invention relates to a method for lowering intraocular pressure in an eye of a mammal suffering from glaucoma comprising administering topically to the eye of the mammal a compound of Formula I

  I wherein R is hydrogen or a pharmaceutically acceptable cation selected from the group consisting of an alkali or alkaline-earth metal and a protonated or quaternized amine, in an amount sufficient to lower intraocular pressure.

The present invention also provides a pharmaceutical formulation for the topical treatment of glaucoma comprising a compound of Formula I, together with a pharmaceutically acceptable carrier, the compound of Formula I being present in an amount sufficient to reduce intraocular pressure when administered topically to the eye.

DETAILED DESCRIPTION OF THE INVENTION

The pharmacological methods of the invention involve the administration of (and the pharmaceutical formulations of the invention comprise) a compound of Formula I above. Trifluoromethanesulfonamide, that is, the compound of Formula I wherein R is hydrogen, is a known compound, its synthesis having been described in, for example, U.S. Pat. No. 2,732,398, incorporated herein by reference. The synthetic method disclosed in that patent involves reacting ammonia with a trifluoromethanesulfonyl halide or trifluoromethanesulfonic anhydride.

Compounds of Formula I wherein R is a pharmaceutically acceptable cation are also generally known or may be prepared using known methods. By "pharmaceutically acceptable cation" is meant alkali or alkaline-earth metal ions and protonated or quaternized amines which, in the concentrations used, have no observable biological activity or toxicity. Such compounds may be readily prepared, since the hydrogen atom of trifluoromethanesulfonamide is relatively acidic and may be replaced, for example, by alkali or alkaline-earth metal ions by neutralization with a salt of a weak acid. Suitable alkali or alkaline-earth metal ions which may be utilized include sodium, potassium magnesium and lithium ions. Further, a hydrogen atom of trifluoromethanesulfonamide may be replaced by inorganic cations such as ammonium (by neutralization with ammonia). Still further, a hydrogen atom of trifluoromethanesulfonamide may be replaced by a protonated or quaternized amine, for example, by neutralizing trifluoromethanesulfonamide with morpholine, benzathine $(PhCH_2NHCH_2CH_2NHCH_2Ph)$, choline hydroxide, diethanolamine, ethylenediamine, meglumine $(HOCH_2CH(OH)CH(OH)CH(OH)CH(OH)CH_2NHCH_3)$, procaine, N-methylpiperazine, or tromethamine$((HOCH_2)_3CNH_2)$.

It is particularly advantageous to use topical administration of an agent to reduce intraocular pressure, because the amount administered can be reduced markedly from the amount necessary when administration is oral. Moreover, topical administration minimizes or eliminates potentially adverse side effects which may result when the agent is administered systemically. For example, trifluoromethanesulfonamide, when administered systemically, is a mild diuretic. Topical administration avoids such action.

Thus, the compounds of the invention will generally be administered as topical ophthalmic formulations such as an ointment, suspension, solution or insert. One skilled in the art is familiar with such formulations. A compound of Formula I will typically be present in an amount of about 0.01 to 15 percent by weight based on the total weight of the formulations. Most preferably, about 0.1 to 3 percent of a compound of Formula I will be present in the formulations. The objective is to administer a dose of from 0.1 to 10 mg per eye per day to the patient, with treatment continuing so long as the condition being treated persists.

An ophthalmic solution is a preferred ophthalmic formulation. In such a presentation, a compound of Formula I is dissolved in a physiologically acceptable, isotonic solution such as an isotonic boric acid solution, an isotonic sodium chloride solution, an isotonic sodium borate solution or the like.

The ophthalmic solution may further comprise a non-ionic surfactant to aid in dissolving of the compound of Formula I, suitable surfactants being polyoxyethylene sorbitan monooleate, polyoxyethylene stearoyl triglyceride, polyethylene glycol, alpha- or beta-cyclodextrin, and the like.

The ophthalmic solution may further comprise a preservative such as a p-hydroxybenzoate ester (e.g., methyl p-hydroxybenzoate or ethyl p-hydroxybenzoate), a cationic surface-active agent (e.g., a benzalkonium chloride), or an alcohol (e.g., benzyl alcohol, chlorobutanol or phenethyl alcohol).

Still further, the ophthalmic solution may comprise a thickener such as polyvinylpyrrolidone, methyl cellulose, hydroxypropyl methyl cellulose, polyvinyl alcohol, or sodium polyacrylate to improve retention of the solution in the conjunctival sac.

Compounds of Formula I which are salts may be used to advantage to adjust the pH of the solution used, or to perhaps provide longer-acting formulations.

Ointments containing a compound of Formula I may be prepared in the conventional way using known excipients such as polyethylene glycol, a cellulose derivative, petroleum jelly, fluid paraffin, polyoxyethylene sorbitan monooleate, polyoxyethylene stearoyl triglyceride or the like. A preservative such as one of those described above may also be included.

The ophthalmic solution and ointment will typically have a pH of about 4 to 8. Beyond these extremes is not generally physiologically acceptable.

While a compound of Formula I will typically be the only active ingredient in an ophthalmic formulation, one or more additional active ingredients such as a beta-blocker (e.g., timolol or carteolol) may also be included.

The ophthalmic formulations are sterilized and provided in a sterilized container, e.g., by bacteria filtration sterilization or compressed steam sterilization. A disposable container or returnable container may be used.

The dosage of a compound of Formula I which will be administered to lower intraocular pressure in a mammal suffering from glaucoma will vary depending upon the disease state, as will be known by the medical practitioner.

The following examples are used to illustrate the invention and are not intended to limit the invention. All amounts given are parts by weight unless otherwise indicated.

EXAMPLE 1

Trifluoromethanesulfonamide (14.9g, 0.10 mole), morpholine (8.7g, 0.10 mole) and acetone (100 ml) were stirred together for one hour. The solvent was evaporated in vacuo to give morpholinium trifluoromethanesulfonamide, m.p. 84°–87° C. Analysis: Calculated for $C_5H_{11}F_3N_2O_3S$: %C 25.4; %H, 4.7; %N, 11.8; found: %C, 25.3;D %H, 4.7; %N, 11.7.

EXAMPLE 2

Trifluoromethanesulfonamide, 40.66 g (0.273 mole), was added to a stirred mixture of sodium hydroxide pellets, 10.91 g (0.273 mole), in 200 ml of methanol. After 15 minutes, the solution was filtered and concentrated to dryness in a rotary evaporator. Further drying at 70° C. at <1 torr gave 43.3 g of sodium trifluoromethanesulfonamide as a white powder, m.p. 221°–224° C. Recrystallization of 10.3 g of this salt from 100 ml of tetrahydrofuran/15 ml diethyl ether afforded 7.3 g of white leaflets, m.p. 224°–226°. Analysis: Calculated for $CHF_3NNaO_2SO$ %C, 7.0; %H, 0.6; %N, 8.2; Found: %C, 7.0; %H, 0.9; %N, 8.0.

EXAMPLE 3

The effect of trifluoromethanesulfonamide on intraocular pressure was studied as follows in an imbibed water-loaded model, and the results were compared with those obtained when N-benzoyltrifluoromethanesulfonamide and N-(n-butyryl)trifluoromethanesulfonamide were studied similarly.

Twelve male white rabbits weighing about 2 kg with no ocular abnormalities were employed in this study. The rabbits were raised in a breeding room conditioned at a temperature of 20°–28° C., and a relative humidity of 40–70%. The rabbits were fed 80g a day of "RC-4" (a feedstuff available from Nippon Kurea, Japan), and were allowed to imbibe water freely. The test drugs were dissolved in distilled water to a concentration of 1.0% by weight immediately before use. Using four rabbits per drug, the above solutions of test drugs were instilled in 50-microliter doses five times at 5-minute intervals into one eye of each rabbit. The untreated eye of each rabbit was similarly dosed with distilled water. Thirty minutes after the first instillation for each rabbit, distilled water prewarmed to 37° C. was administered via a stomach tube in an amount of 75 mg per kg.

Intraocular pressure for both the drug-treated eye and control eye of each rabbit was measured at 0.5, 1.0 and 2 hours after administration of water to the stomach. Measurement was conducted using a pneumotonograph (available from Alcon Corporation, Ft. Worth, Tex.). In order to carry out this measurement, the eye was first anesthetized by instillation of 0.4% oxybuprocaine hydrochloride (available under the trade name "Anelocal" from Senju Pharmaceutical Co., Ltd., Japan). For each rabbit, the difference in intraocular pressure between the drug-treated eye and control eye was determined. The results were as shown in TABLE I below with each value representing the average intraocular pressure observed for the four animals treated with each test drug plus or minus the standard deviation.

TABLE I

| | Effect of Test Compounds on Ocular Hypertensive Rabbits Orally Pretreated with Distilled water (mm Hg mean ± S. D.) | | | | | |
|---|---|---|---|---|---|---|
| Time (hr.) | Trifluoromethane-sulfonamide n = 4 | Control | N—benzoyltri-fluoromethane-sulfonamide n = 4 | Control | N—(n-butyryl)-trifluoro-methane-sulfonamide n = 4 | Control |
| Before instillation | 23.5 ± 1.5 | 23.5 ± 1.5 | 22.0 ± 1.2 | 21.8 ± 1.1 | 22.0 ± 1.0 | 21.8 ± 1.3 |
| 0 | 21.5 ± 2.2 | 23.3 ± 2.4 | 20.8 ± 1.2 | 20.8 ± 1.1 | 19.3 ± 0.8 | 20.0 ± 1.1 |
| 0.5 | 29.5 ± 1.9** | 34.5 ± 2.4 | 29.8 ± 1.5 | 29.8 ± 1.3 | 29.0 ± 0.9 | 29.0 ± 0.9 |
| 1 | 26.8 ± 1.8** | 31.8 ± 2.2 | 25.8 ± 2.6 | 25.5 ± 2.2 | 25.5 ± 1.3 | 25.5 ± 1.3 |

TABLE I-continued

Effect of Test Compounds on Ocular Hypertensive Rabbits Orally Pretreated with Distilled water (mm Hg mean ± S. D.)

| Time (hr.) | Trifluoromethane-sulfonamide n = 4 | Control | N—benzoyltri-fluoromethane-sulfonamide n = 4 | Control | N—(n-butyryl)-trifluoro-methane-sulfonamide n = 4 | Control |
|---|---|---|---|---|---|---|
| 2 | 20.5 ± 3.0* | 23.8 ± 2.3 | 20.0 ± 2.5 | 19.8 ± 2.6 | 22.8 ± 0.9 | 22.3 ± 0.7 |

Notes:
Marks * and ** denote values which are significantly different at confidence levels of $p < 0.05$ and $p < 0.02$, respectively, fr n the control.

As can be seen from TABLE I, trifluoromethanesulfonamide, when compared to the control, significantly inhibited the increase in intraocular pressure by about 5 mm Hg at 0.5 and 1 hour after administration of water, and by about 3 mm Hg at 2 hours. N-benzoyltrifluoromethanesulfonamide and N-(n-butyryl)trifluoromethanesulfonamide, on the other hand, did not significantly inhibit the increase in intraocular pressure.

In an alternative assay, the effect of trifluoromethanesulfonamide on normal intraocular pressure was measured. The above solution of trifluoromethanesulfonamide in distilled water was instilled in a dose of 50-microliters five times at 5-minute intervals in one eye of each of three rabbits. The untreated eye of each rabbit was dosed with isotonic saline. The intraocular pressure of both the drug-treated eye and the control eye of each rabbit was measured as described above at 0.5, 1, 2 and 4 hours after the first instillation of drug or isotonic saline. Intraocular pressure was measured as before. In this test, the reference compound, acetazolamide, was administered as a 10% solution in distilled water to one eye of each of three rabbits, with isotonic saline again being administered to the control eyes.

Results are shown in TABLE II, each value again representing the average intraocular pressure for the three animals tested with each test drug, plus or minus the standard deviation.

TABLE II

Effect of Trifluoromethanesulfonamide and Acetazolamide on Intraocular Tension in Ocular Normotensive Rabbits (mm Hg, mean ± S. D.)

| Time (hr.) | Trifluoro-methane-Sulfonamide | Control | Acetazol-amide | Control |
|---|---|---|---|---|
| Before instillation | 23.3 ± 0.6 | 22.3 ± 0.6 | 19.0 ± 0.8 | 18.3 ± 1.3 |
| 0.5 | 18.7 ± 0.6*** | 21.7 ± 1.5 | 18.8 ± 0.8 | 17.8 ± 1.1 |
| 1 | 18.3 ± 2.1** | 21.0 ± 1.0 | 17.8 ± 0.9 | 16.8 ± 1.5 |
| 2 | 19.7 ± 0.6* | 22.0 ± 1.0 | 18.5 ± 0.9 | 17.8 ± 1.5 |
| 4 | 23.3 ± 1.2 | 23.0 ± 0 | 18.8 ± 0.9 | 17.8 ± 1.5 |

Notes:
The asterisks *, , and * denote values which are significantly different from the control at confidence levels of $p < 0.05$, $p < 0.01$, $p < 0.001$, respectively.

As can be seen from TABLE II, trifluoromethanesulfonamide, when compared to the control, decreased intraocular pressure significantly at 0.5, 1 and 2 hours. Acetazolamide, on the other hand, did not significantly decrease intraocular pressure.

EXAMPLE 4

Morpholinium trifluoromethanesulfonamide was studied in ocular normotensive rabbits generally following the procedure of E 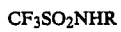 A two percent solution of the compound in distilled 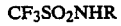 was observed to cause a statistically significant re<sub>.</sub> n in intraocular pressure compared to control at 0.5, 1 and 2 hours.

EXAMPLE 5

Sodium trifluoromethanesulfonamide was studied in ocular normotensive rabbits generally following the procedure of Example 3. A two percent solution of the compound in distilled water was observed to cause a statistically significant reduction in intraocular pressure between treatment and control changes from baseline at 0.5 hour ($p < 0.05$), but not at 1 or 2 hours.

What is claimed is:

1. A method for lowering intraocular pressure in an eye of a mammal suffering from glaucoma, comprising administering topically to said eye a compound of the formula $$CF_3SO_2NHR$$

wherein R is hydrogen or a pharmaceutically acceptable cation selected from the group consisting of an alkali or alkaline-earth metal ion and a protonated or quaternized amine, in an amount sufficient to reduce intraocular pressure.

2. A method according to claim 1, wherein said compound is administered topically to the eye.

3. A method according to claim 2, wherein R is a protonated or quaternized amine.

4. A method according to claim 1, wherein said compound is trifluoromethanesulfonamide.

5. A method according to claim 2, wherein said compound is trifluoromethanesulfonamide.

6. A topical pharmaceutical formulation for lowering intraocular pressure in a mammal suffering from glaucoma, comprising a compound of the formula $$CF_3SO_2NHR$$

wherein R is hydrogen or a pharmaceutically acceptable cation selected from the group consisting of an alkali or alkaline-earth metal ion and a protonated or quaternized amine, dissolved in a physiologically acceptable, isotonic solution, said compound being present in said solution in an amount sufficient to lower intraocular pressure when said formulation is applied topically to the eye.

7. A pharmaceutical formulation according to claim 6, wherein said compound is trifluoromethanesulfonamide.

* * * * *

UNITED STATES PATENT AND TRADEMARK OFFICE
CERTIFICATE OF CORRECTION

PATENT NO. : 4,824,866

DATED : April 25, 1989

INVENTOR(S) : Donald C. Kvam

It is certified that error appears in the above-identified patent and that said Letters Patent is hereby corrected as shown below:

Col. 3, line 54    "in vacuo" should read --in vacuo--.

Col. 4, line 2     "found:  %C, 25.3;D %H, 4.7;  should read --found:  %C, 25.3; %H, 4.7;--

Col 4, line 15     "CHF$_3$NNaO$_2$SO" should read --CHF$_3$NNaO$_2$S:---

Signed and Sealed this

Twenty-fifth Day of July, 1989

Attest:

DONALD J. QUIGG

Attesting Officer

Commissioner of Patents and Trademarks